United States Patent
Parker et al.

(10) Patent No.: US 6,820,497 B2
(45) Date of Patent: Nov. 23, 2004

(54) METHOD AND APPARATUS FOR DETECTING AND CONTROLLING ORIENTATION OF ARTICLES FOR FURTHER PROCESSING

(75) Inventors: Jeffrey W. Parker, Old Fort, NC (US); Marty Juliano, Stuart, FL (US)

(73) Assignee: Threadbear, LLC, Old Fort, NC (US)

( * ) Notice: Subject to any disclaimer, the term of this patent is extended or adjusted under 35 U.S.C. 154(b) by 301 days.

(21) Appl. No.: 10/037,818

(22) Filed: Jan. 2, 2002

(65) Prior Publication Data

US 2002/0104857 A1 Aug. 8, 2002

Related U.S. Application Data

(60) Provisional application No. 60/259,457, filed on Jan. 3, 2001.

(51) Int. Cl.[7] .................................................. G01N 3/08
(52) U.S. Cl. .............................. 73/831; 73/862.39; 73/3
(58) Field of Search ........................ 73/826, 828, 831, 73/834, 835, 862.393, 818, 819

(56) References Cited

U.S. PATENT DOCUMENTS

| 3,639,987 | A | * | 2/1972 | Page ............................ 33/2 A |
| 5,040,475 | A | | 8/1991 | Fournier et al. ......... 112/121.15 |
| 5,058,516 | A | | 10/1991 | Maegawa et al. ....... 112/121.12 |
| 5,094,110 | A | * | 3/1992 | Porter et al. ................... 73/832 |
| 5,165,355 | A | | 11/1992 | Fournier et al. .......... 112/262.2 |
| 5,456,392 | A | | 10/1995 | Majors ......................... 223/112 |
| 5,477,996 | A | | 12/1995 | Migliorini .................... 223/112 |
| 5,511,501 | A | | 4/1996 | Bell et al. .............. 112/470.15 |
| 5,651,483 | A | | 7/1997 | Bell et al. .................... 223/112 |
| 5,769,286 | A | | 6/1998 | Conti ............................. 223/75 |
| 5,771,830 | A | | 6/1998 | Hodges ................. 112/470.15 |
| 5,884,822 | A | | 3/1999 | Migliorini ....................... 223/1 |
| 5,941,431 | A | | 8/1999 | Parker .......................... 223/112 |
| 5,992,712 | A | | 11/1999 | Nishikawa et al. ............. 223/1 |
| 6,003,345 | A | | 12/1999 | Jordan ........................... 66/215 |
| 6,338,723 | B1 | * | 1/2002 | Carpenter et al. ............. 602/75 |

FOREIGN PATENT DOCUMENTS

WO        WO 98/35081        8/1998

* cited by examiner

Primary Examiner—Max Noori
(74) Attorney, Agent, or Firm—Kennedy Covington Lobdell & Hickman, LLP

(57) ABSTRACT

An apparatus and method for use in a system for handling a flaccid article, such as a sock or other hosiery item, having portions of differing stretch characteristics, by which the differentially stretchable portions may be distinguished from one another by applying a stretching force to one of the portions and then detecting the degree of stretch, resistance to stretch, or other reaction of the stretched portion in response to the stretching force, whereby an indication is derived as to which of the differentially stretchable portions was stretched.

23 Claims, 1 Drawing Sheet

METHOD AND APPARATUS FOR DETECTING AND CONTROLLING ORIENTATION OF ARTICLES FOR FURTHER PROCESSING

CROSS-REFERENCE TO RELATED APPLICATION

This application is entitled to the benefit of, and claims priority to, U.S. Provisional Patent Application Ser. No. 60/259,457, filed Jan. 3, 2001, entitled "METHOD AND APPARATUS FOR DETECTING AND CONTROLLING ORIENTATION OF ARTICLES FOR FURTHER PROCESSING."

BACKGROUND OF THE INVENTION

The present invention relates generally to article handling apparatus and methods and, more particularly, to a novel method and apparatus for handling articles having opposite ends or other portions having differing stretch characteristics.

Across substantially all industries, the desire to improve efficiency and productivity while at the same time to reduce costs has provided the impetus for an ever increasing automation of various manufacturing steps. Nevertheless, the automated handling of manufactured articles having a flaccid character presents considerable difficulty. By way of example but without limitation, the textile industry has been successful in automating many of the steps in the manufacture and processing of socks and other hosiery articles, but it still largely remains necessary for human operators to perform various steps in the overall manufacturing operation, such as manually placing hosiery articles on the forms of a hosiery boarding machine.

One of the fundamental difficulties in automating the handling of flaccid articles such as hosiery is that the flaccid character of the articles makes it difficult, if not impossible, to maintain the articles in a consistently uniform orientation while being transported or otherwise handled. For example, the vast majority of conventional hosiery articles are made of circularly knitted fabric initially produced in a tubular form commonly referred to as a "blank" which, in most cases, has a distinct toe portion at one tubular end and a differently fashioned cuff portion at the opposite tubular end. In the handling of such articles subsequent to the initial knitting of the tubular blank, it is therefore important, if not critical, that the toe and cuff ends be differentiated. For example, in order to sew closed the toe end portion of a hosiery blank, it is essential that the toe end rather than the cuff end be presented to the sewing device. Conventionally, the feeding or placement of a hosiery article in correct orientation for such operations is performed manually, despite the significant labor cost such a manual operation adds to the overall hosiery manufacturing process.

Accordingly, a substantial need exists within not only the textile industry but substantially any industry involved in the manufacture or other handling of flaccid articles such as hosiery to automate the function of uniformly orienting such articles and, in particular, to automate the threshold step of recognizing different portions of such articles which have distinguishing physical characteristics.

SUMMARY OF THE INVENTION

It is accordingly an object of the present invention to provide a novel method and apparatus for automatically distinguishing from one another physically differing portions of the article. A more particular object of the present invention is to provide a novel method and apparatus by which differing portions of an article having differential stretch characteristics may be automatically distinguished from one another. A further object of the present invention is to provide a method and apparatus by which the opposite ends of a hosiery article may be distinguished from one another as a result of their respectively differing stretch characteristics.

Briefly summarized, the present invention addresses these objectives by providing a method and apparatus basically operable to apply a stretching force to one of first and second differentially stretchable portions of an article and to detect a reaction of the one portion in response to the stretching force to obtain an indication of which of the first and second portions was stretched.

In a preferred embodiment of the present method and apparatus, the stretching force is applied by a device operative to grasp the one portion of the article at spaced locations thereon and to move the spaced locations further apart. The reaction of the one portion of the article to the stretching force may preferably be detected by a sensor which detects the amount by which the article stretches or the resistance of the article to the stretching force. A controller preferably compares the reaction of the article to a predetermined set of reactive values corresponding to the respective first and second portions of the article.

One advantageous embodiment of the method and apparatus is in a system having a transport structure for conveying a plurality of the articles in sequence, with each article being randomly oriented with its first or second portion in a relatively leading disposition and the other portion in a relatively trailing disposition. Each article within the transport structure is presented in sequence to a processing station at which the stretching force is applied to the leading or trailing end of each article. Preferably, a suitable arrangement is provided for controlling the subsequent handling of each article in response to the sensor or other device detecting the manner in which the article reacts to the stretching force. For example, each article with its first portion in a leading disposition may be handled in one manner for subsequent processing, while each article having its second portion in a leading disposition may be handled in a different manner for subsequent processing.

A particularly advantageous application of the present method and apparatus is in a system for handling textile goods, especially hosiery items having a toe end and a cuff end of differing stretch characteristics. The method and apparatus may be arranged such that each hosiery item having the toe end in a leading disposition is simply permitted to continue in the same orientation along the transport structure, but each hosiery item having its cuff end in a leading disposition is reversed before continuing conveyance within the transport structure.

These and other features, details and advantages of the present apparatus and method will be recognized and understood by those persons skilled in the relevant art from the following detailed disclosure of the invention with reference to the accompanying drawing.

BRIEF DESCRIPTION OF THE DRAWING

The single accompanying drawing is a schematic diagram of the present method and apparatus as preferably embodied in a system for handling hosiery articles.

DETAILED DESCRIPTION OF THE PREFERRED EMBODIMENT

Figure 1:
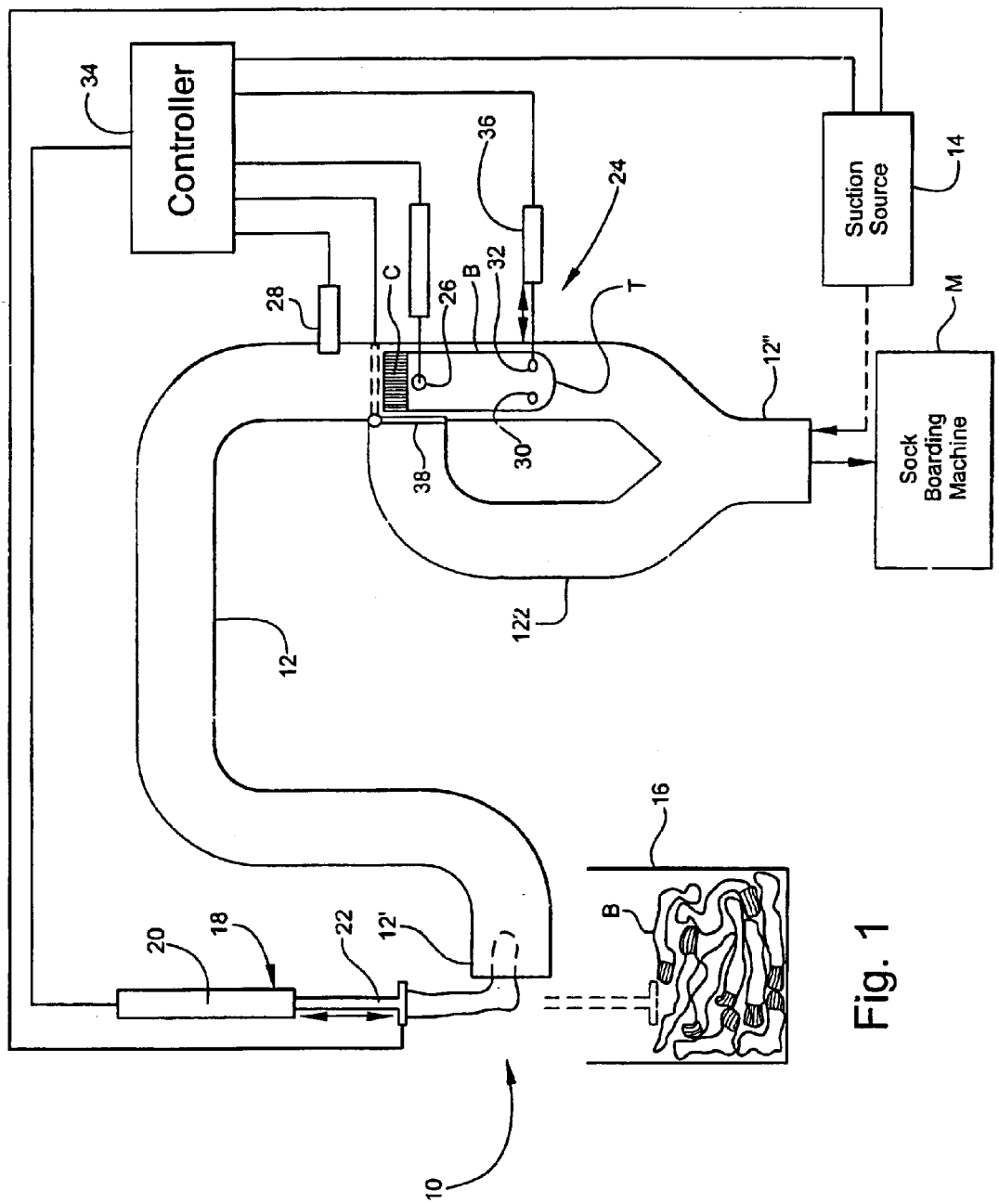

Referring now to the accompanying drawing, a system for pneumatically conveying hosiery articles such as sock blanks B to a sock boarding machine M is depicted in schematic diagram form, the overall system being indicated as a whole by the referenced numeral 10. However, while the present invention is herein illustrated and described in such embodiment, it is to be expressly understood that the present invention is not limited to systems for handling hosiery items, nor is the present invention necessarily limited to the handling of similar textile goods. Rather, it is contemplated that the present invention may have more general application in the textile industry as well as in other industries where a need exists for distinguishing portions of an article by detection of differential stretch characteristics.

As is well known within the hosiery manufacturing industry, such sock blanks B are characteristically fabricated by circular knitting in the form of a seamless knitted tube having a distinct toe portion T and a distinct cuff portion C at the opposite axial ends of the tubular blank B. As will be more fully explained and understood from the following disclosure, the present invention is based on the recognition that the toe and cuff portions T,C of such sock blanks B have differing stretch characteristics because of the differing stitch construction used in fabricating these portions of the blanks B, the cuff portion C characteristically being capable of being stretched to a greater degree transversely (i.e., coursewise) of the axial lengthwise extent of the blank B than the toe portion T.

The hosiery handling system 10 basically comprises a pneumatic conduit arrangement 12 connected to a suction fan or other suitable source of suction, indicated only diagrammatically at 14, and extending between an entrance end 12' adjacent a collection basket, hopper or other suitable container, indicated only schematically at 16, for holding a supply of sock blanks B or other hosiery articles and a discharge end 12" adjacent a downstream station for processing the sock blanks B, such as the loading station of the sock boarding machine M. As will be understood, the suction source 14 establishes a prevailing negative pressure within the conduit arrangement 12 operative to cause sock blanks B to be conveyed from the entrance end 12' to the discharge end 12".

A suitable device is provided for picking an individual sock blank B from the container 16 and presenting the blank B to the entrance end 12' of the pneumatic conduit arrangement 12, as schematically depicted generally at 18. Many possible mechanisms and/or devices may be used as the sock picker device 18. For sake of illustration, but without limitation, the picker device 18 is depicted as comprising a vertically reciprocable linear actuator 20, e.g., a piston and cylinder assembly, having an extending and retracting arm 22 supplied with a pneumatic suction, e.g., from the same suction source 14, for pneumatically grasping individual sock blanks B when extended into the container 16.

As will thus be understood, the picker device 18 is operative upon each reciprocation of its arm 22 to randomly pick a single sock blank B from the container 16 and, in particular, the portion of each individual sock blank B which is aspirated by the picker arm 22 will likewise be random and uncontrolled. Hence, the picker an-n 22 occasionally will pneumatically grasp a sock blank B by its toe end T, or by its cuff end C, or at a location intermediate the ends. The linear travel of the picker arm 22 by the linear actuator 18 is sufficient to retract upwardly from the container 16 to a point elevated above the entrance end 12' of the pneumatic conduit arrangement 12 such that each sock blank B will hang gravitationally from the picker arm 22, whereby regardless of the portion of a sock blank B aspirated by the picker arm 22, a depending end of each sock blank B will be presented to the entrance end 12' of the pneumatic conduit arrangement 12. Thus, each sock blank B will be pneumatically aspirated into the conduit arrangement 12 with either its toe end T or its cuff end C in a relatively leading disposition and the other end in a relatively trailing disposition and the sock blank B will be conveyed through the conduit arrangement 12 in such orientation. Hence, some sock blanks B will necessarily travel through the conduit arrangement 12 with their respective toe ends T in a leading disposition while other sock blanks B will be conveyed with their respective cuff ends C in leading disposition.

A sock blank processing station, generally indicated overall at 24, is provided intermediately along the lengthwise extent of the pneumatic conduit arrangement 12 and, as more fully explained below, is operable to detect whether each sock blank B transported through the conduit arrangement 12 in sequence is oriented with its toe end T or its cuff end C in a leading disposition relative to the other end and, if necessary, to reorient any individual sock blank B to reverse its leading and trailing ends as it travels downstream through the conduit arrangement 12 from the processing station 24.

The processing station 24 includes a clamping device, shown only schematically at 26, having an extendable and retractable plunger projecting through the wall of the conduit arrangement 12 by which an individual sock blank B traveling through the conduit arrangement 12 may be stopped and clamped at the processing station by extension of the plunger and subsequently a clamped sock blank B may be released for further conveyance through the conduit arrangement 12 upon retraction of the plunger. Immediately upstream of the clamping device 26 is a sensor 28, e.g., in the form of an electric eye, operative to detect the passage of each sock blank B in sequence traveling through the conduit arrangement 12. Each of the clamping device 26 and the sensor 28 are operatively connected to a controller 34, e.g., a programmable microprocessor or other suitable programmable control device. The controller 34 is programmed to actuate the clamping device 24 in a predetermined timed relationship with each detection by the sensor 28 of the passage of a sock blank B, thereby to clamp the sock blank B at a location generally adjacent its trailing end in its conveyed orientation, as is schematically depicted in the drawing.

Another pair of clamping devices 30, 32 of similar construction and operation to that of the clamping device 26 are disposed at the processing station 24 downstream of the clamping device 26 by a predetermined distance less than the average length of the sock blanks B. Each of the clamping devices 30, 32 similarly have a respective plunger element arranged to be extendable and retractable through the wall of the conduit arrangement 12 for selective clamping engagement with the leading end of a sock blank B when clamped upstream by the clamping device 26. For such purpose, the clamping devices 30, 32 are also operatively connected to the controller 34 for operation in timed relationship with the clamping device 26.

As aforementioned, the present invention is based on the recognition that the cuff end C and the toe end T of a typical conventional sock blank B have differential stretch characteristics, the cuff end typically having a greater degree of stretchability in the coursewise, i.e., widthwise, direction, whereby the toe and cuff ends T, C of a sock blank B may be distinguished by stretching either end and comparing the stretch response to a predetermined set of stretch characteristics for the particular form of hosiery blank B being handled. Accordingly, the clamping elements 30, 32 at the processing station 24 are also arranged for one or both of the clamping elements 30, 32 to be movable toward and away from the other under the control of the controller 34, as schematically represented by the directional arrow in the drawing, thereby to impose a stretching force on the leading end of each hosiery blank B when clamped at the processing station 24.

A sensor 36 is associated with the movable clamping element 30, 32 to measure a predetermined characteristic of the movement of the clamping element indicative of the degree to which the leading end of the sock blank B is thereby stretched. For example, the sensor 36 may measure the length of travel of the movable clamping element 30 or 32 as an indication of the amount by which the leading end of the hosiery blank B stretches. Alternatively, the sensor 36 may measure a stress characteristic in the actuating mechanism for imparting movement to the clamping element 30 or 32 as an indication of the resistance of the leading end of the article to the imposed stretching force. Other alternative means of sensing the degree to which the leading end of the hosiery blank B is stretched may also be utilized. In either case, the sensor 36 transmits a proportional signal to the controller 34 which compares the measurement made by the sensor 36 against a set of values stored in the memory of the controller 34 representing the relative respective stretch characteristics of the average toe end T and the average cuff end C for the type of sock blank B being conveyed, whereby the programmed processing capability of the controller 34 enables a conclusion to be drawn as to whether the toe end T or the cuff end C of the hosiery blank B is in a leading disposition.

Depending upon the downstream location to which the sock blanks B are being conveyed, it may be desired that the sock blanks B are presented with their toe ends T or their cuff ends C in a leading disposition. For example, a typical sock boarding machine M will require the cuff end of a sock blank B to be placed first onto the boards or forms of the machine, whereby it will be preferred that the cuff end be oriented in a leading disposition for the conveyance of each sock blank B to the machine. In any event, the sock blanks B must be oriented in a uniform disposition for presentation to the downstream machine. Hence, inasmuch as the sock blanks B will be randomly presented to the processing station 24 with some sock blanks B having their toe ends T in a leading disposition and other sock blanks B having their cuff ends C in a leading disposition, the processing station 24 includes the capability of reversing the toe and cuff ends of any individual sock blank B which is detected by the controller 34 as not being in the desired orientation.

Specifically, a secondary conduit leg 122 branches from the main pneumatic conduit arrangement 12 at a location adjacent the upstream clamping device 26 and extends therefrom to a location downstream at which the secondary conduit leg 122 merges again with the main extent of the pneumatic conduit arrangement 12. A suitable valve or other form of closure device, only schematically indicated at 38, is disposed at the juncture between the secondary conduit leg 122 and the main conduit arrangement 12 for movement between a position closing the entrance to the secondary conduit leg 122, as depicted in full lines in the drawing, and a position opening the entrance to the secondary conduit leg 122 while closing the main conduit arrangement 12, as depicted in broken lines in the drawing.

When the controller 34 detects that a sock blank B clamped at the processing station 24 is in an incorrect orientation, i.e., the sock blank B has the incorrect end in a leading disposition, then the controller 34 actuates the movement of the closure 38 to open the entrance to the secondary conduit leg 122, whereby the suction prevailing in the pneumatic conduit arrangement 12 is then primarily applied through the secondary conduit leg 122. Upon release of the clamping devices 26, 30, 32, the sock blank B will then be aspirated into the secondary conduit leg 122 rather than continuing its initial conveyance through the primary conduit arrangement 12. Thus, the previously trailing end of the sock blank B becomes the leading end thereof as the sock blank B travels through the secondary conduit leg 122 and, hence, when the secondary conduit leg 122 merges with the main conduit arrangement 12, the sock blank B will be in the correct orientation for presentation to the downstream sock boarding or other machine M.

On the other hand, when the controller 34 recognizes the presence of a sock blank B in the correct orientation, the controller 34 does not actuate the closure 38, leaving the closure 38 in a disposition closing the entrance to the secondary conduit leg 122. Thus, upon release of the clamping devices 26, 30, 32, the sock blank B continues under the pneumatic aspiration of the suction source 14 to travel through the conduit arrangement 12 in the same original orientation as presented to the processing station 34.

Those persons skilled in the art will readily recognize the significant advantages of the present invention by enabling randomly traveling sock blanks to be detected as to their traveling orientation and, as necessary, to be reoriented for uniform delivery and presentation to a downstream machine. Thus, the present invention will enable many operations currently performed by hand, such as the manual placement of socks on a sock boarding machine, to be fully automated, thereby improving efficiency and productivity and lowering if not substantially eliminating associated labor costs. More broadly, it will be recognized and understood that the present invention will enable similar automation of the handling of the flaccid articles.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. In a system for handling an article having first and second portions of differing stretch characteristics, wherein the system comprises conveying a plurality of the articles in sequence with each article being randomly oriented with one of the first and second portions in a relatively leading disposition and the other of the first and second portions in a relatively trailing disposition, a method for distinguishing the first and second portions from one another, the method comprising applying a stretching force to one of the first and second portions of the article and detecting a reaction of the one portion in response to the stretching force as an indication of which of the first and second portions was stretched.

2. The method according to claim 1, wherein the applying of a stretching force comprises grasping the one portion of the article at spaced locations thereon and moving at least one of the spaced locations further apart.

3. The method according to claim 1, wherein the detecting of a reaction comprises sensing an amount by which the article stretches in response to the stretching force.

4. The method according to claim 1, wherein the detecting of a reaction comprises sensing a resistance of the article to the stretching force.

5. The method according to claim 1, wherein the detecting of a reaction comprises comparing the reaction to a predetermined set of reaction values corresponding to the respective first and second portions of the article.

6. The method according to claim 1, wherein the system further comprises presenting each article of the plurality of articles in sequence to a processing station whereat the stretching force is applied to the leading and/or the trailing end of each article.

7. The method according to claim 6, and further comprising handling each article with the first portion thereof in leading disposition in one manner for subsequent processing and handling each article with the second portion thereof in leading disposition in another manner for subsequent processing.

8. The method according to claim 7, and further comprising reorienting each article with the second portion thereof in leading disposition to reverse the leading and trailing ends thereof.

9. The method according to claim 1, and further comprising controlling an orientation of the article for subsequent processing according to the detecting of a reaction to the stretching force.

10. The method according to claim 1, wherein the article is a textile good.

11. The method according to claim 1, wherein the article is a hosiery item having a toe end and a cuff end of differing stretch characteristics.

12. In a system for handling an article having first and second portions of differing stretch characteristics, the system comprising a transport structure for conveying a plurality of the articles in sequence with each article being randomly oriented with one of the first and second portions in a relatively leading disposition and the other of the first and second portions in a relatively trailing disposition, the transport structure including a processing station to which each article of the plurality of articles is presented in sequence, apparatus for distinguishing the first and second portions from one another, the apparatus comprising a device disposed at the processing station for applying a stretching force to one of the first and second portions of the article and a device for detecting a reaction of the one portion in response to the stretching force as an indication of which of the first and second portions was stretched.

13. The apparatus according to claim 12, wherein the stretching force applying device comprises elements for grasping the one portion of the article at spaced locations thereon and for moving at least one of the elements further apart from the spaced locations.

14. The apparatus according to claim 12, wherein the reaction detecting device comprises a detector for sensing an amount by which the article stretches in response to the stretching force.

15. The apparatus according to claim 12, wherein the reaction detecting device comprises a detector for sensing a resistance of the article to the stretching force.

16. The apparatus according to claim 12, wherein the reaction detecting device comprises a controller for comparing the reaction to a predetermined set of reaction values corresponding to the respective first and second portions of the article.

17. The apparatus according to claim 12, and further comprising an arrangement for handling each article with the first portion thereof in leading disposition in one manner for subsequent processing and for handling each article with the second portion thereof in leading disposition in another manner for subsequent processing.

18. The apparatus according to claim 17, wherein the arrangement further comprises a device for reorienting each article with the second portion thereof in leading disposition to reverse the leading and trailing ends thereof.

19. The apparatus according to claim 12, and further comprising an arrangement for controlling an orientation of the article for subsequent processing in response to the reaction detecting device.

20. The apparatus according to claim 12, wherein the article is a textile good.

21. The apparatus according to claim 12, wherein the article is a hosiery item.

22. In a system for handling an article having first and second portions of differing stretch characteristics, a method for distinguishing the first and second portions from one another, the method comprising applying a stretching force to one of the first and second portions of the article, detecting a reaction of the one portion in response to the stretching force as an indication of which of the first and second portions was stretched, and controlling an orientation of the article for subsequent processing according to the detecting of a reaction to the stretching force.

23. In a system for handling an article having first and second portions of differing stretch characteristics, apparatus for distinguishing the first and second portions from one another, the apparatus comprising a device for applying a stretching force to one of the first and second portions of the article and a device for detecting a reaction of the one portion in response to the stretching force as an indication of which of the first and second portions was stretched, and an arrangement for controlling an orientation of the article for subsequent processing in response to the reaction detecting device.

* * * * *